(12) United States Patent
Suh et al.

(10) Patent No.: US 11,633,289 B2
(45) Date of Patent: Apr. 25, 2023

(54) MODULAR FOOTPRINT CAGE SYSTEM

(71) Applicant: CTL Medical Corporation, Addison, TX (US)

(72) Inventors: Sean Suh, Milltown, NJ (US); Jon Suh, Ambler, PA (US)

(73) Assignee: CTL Medical Corporation, Addison, TX (US)

( * ) Notice: Subject to any disclaimer, the term of this patent is extended or adjusted under 35 U.S.C. 154(b) by 690 days.

(21) Appl. No.: 16/688,791

(22) Filed: Nov. 19, 2019

(65) Prior Publication Data

US 2020/0085587 A1    Mar. 19, 2020

Related U.S. Application Data

(63) Continuation-in-part of application No. 16/291,278, filed on Mar. 4, 2019, now Pat. No. 11,026,801, which is a continuation of application No. 15/244,868, filed on Aug. 23, 2016, now Pat. No. 10,219,912.

(60) Provisional application No. 62/769,450, filed on Nov. 19, 2018, provisional application No. 62/270,141, filed on Dec. 21, 2015.

(51) Int. Cl.
*A61F 2/44* (2006.01)
*A61F 2/30* (2006.01)

(52) U.S. Cl.
CPC ............ *A61F 2/4455* (2013.01); *A61F 2/447* (2013.01); *A61F 2002/3008* (2013.01); *A61F 2002/30014* (2013.01); *A61F 2002/30092* (2013.01); *A61F 2002/3093* (2013.01); *A61F 2002/30383* (2013.01); *A61F 2002/30448* (2013.01); *A61F 2002/30471* (2013.01); *A61F 2002/30538* (2013.01); *A61F 2002/30578* (2013.01); *A61F 2002/30593* (2013.01); *A61F 2002/30604* (2013.01); *A61F 2002/30616* (2013.01); *A61F 2002/30785* (2013.01); *A61F 2002/30787* (2013.01); *A61F 2002/30841* (2013.01); *A61F 2002/30881* (2013.01); *A61F 2002/30904* (2013.01); *A61F 2220/0016* (2013.01)

(58) Field of Classification Search
CPC .............................. A61F 2/4455; A61F 2/447
See application file for complete search history.

(56) References Cited

U.S. PATENT DOCUMENTS

| | | | |
|---|---|---|---|
| 8,657,882 B2* | 2/2014 | Bonin, Jr. | A61F 2/44 623/17.11 |
| 2007/0179610 A1* | 8/2007 | Biedermann | G02F 1/13458 623/16.11 |
| 2011/0319999 A1* | 12/2011 | O'Neil | A61F 2/4455 623/17.16 |

* cited by examiner

*Primary Examiner* — Andrew Yang
(74) *Attorney, Agent, or Firm* — Brainspark Associates, LLC

(57) ABSTRACT

Disclosed are devices for the fixation and support of vertebrae, particularly adjustable spinal implant devices.

20 Claims, 20 Drawing Sheets

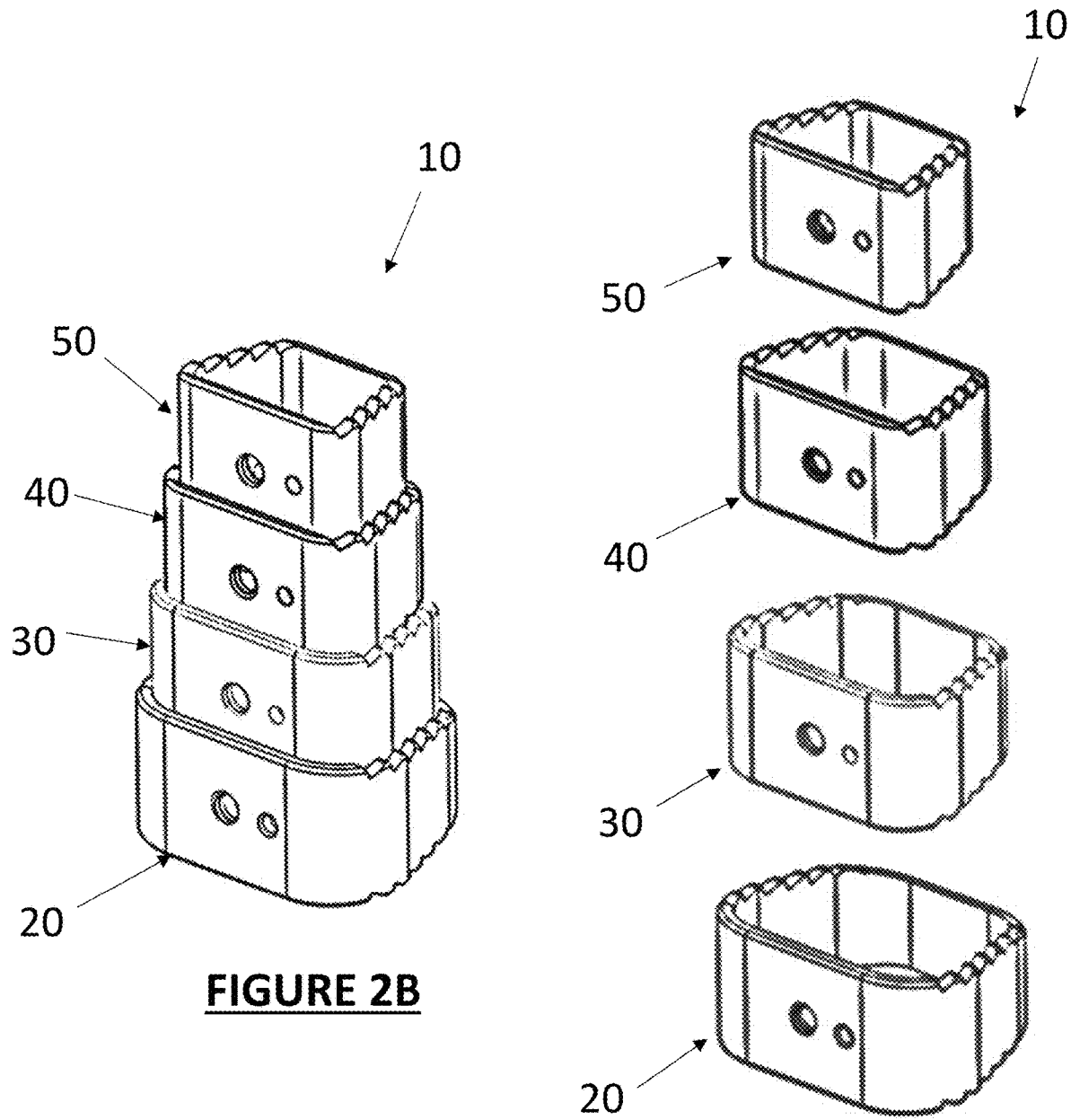

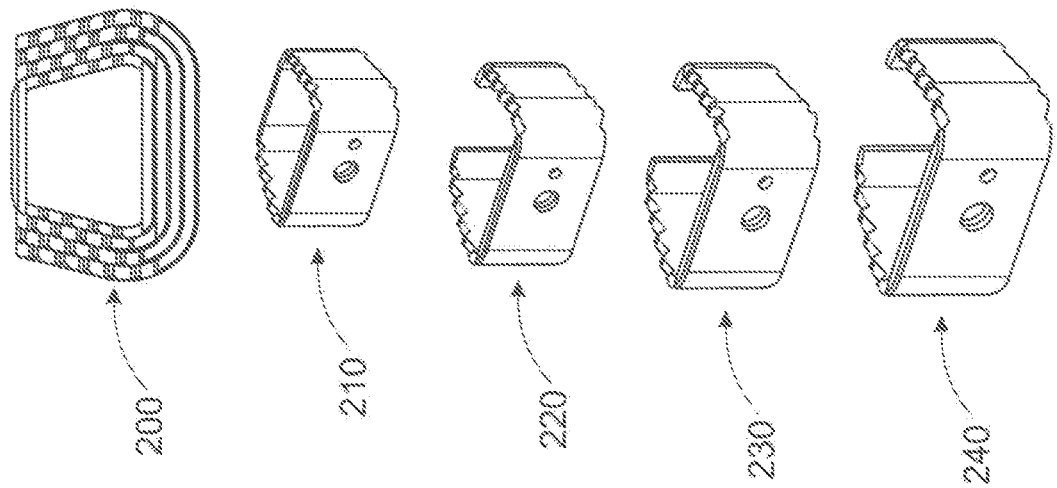
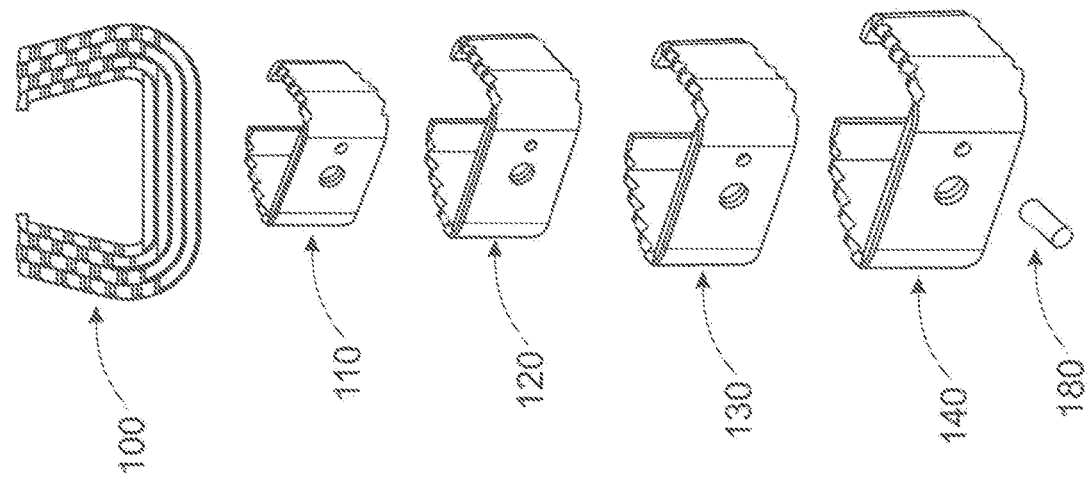
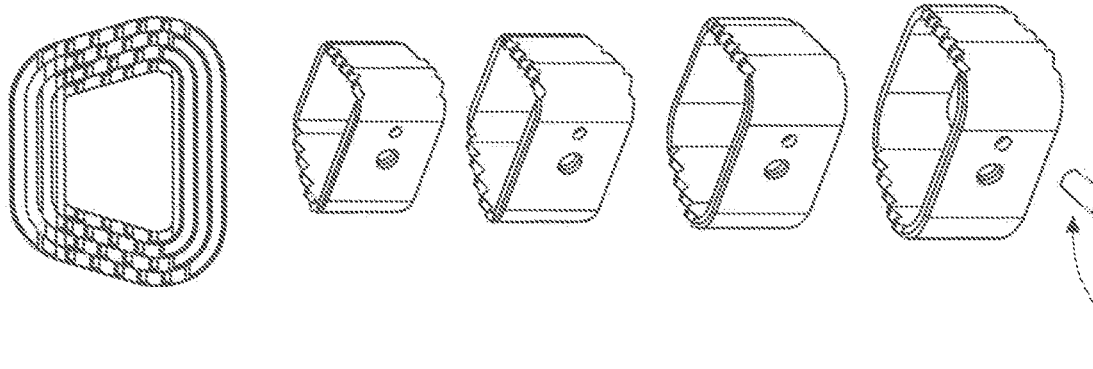

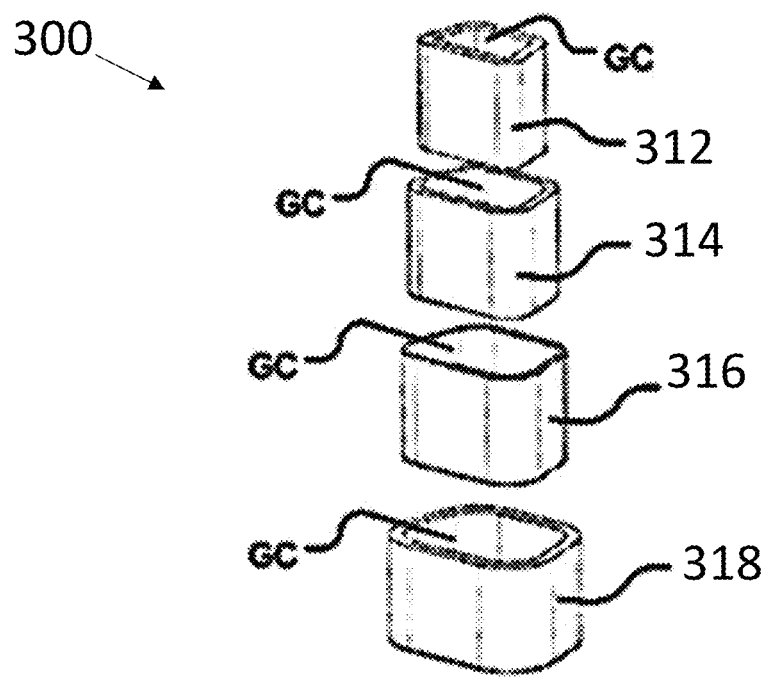
FIGURE 3D
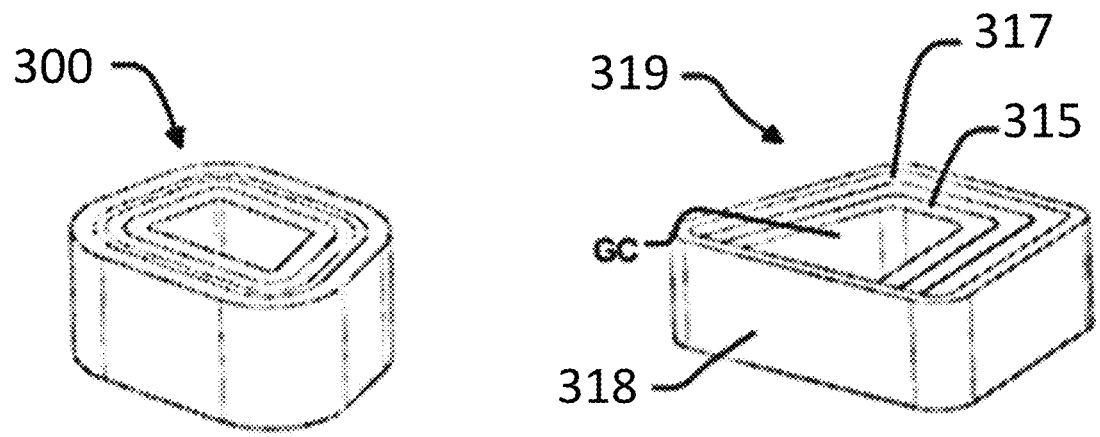
FIGURE 3E
FIGURE 3F

MODULAR FOOTPRINT CAGE SYSTEM

CROSS-REFERENCE TO RELATED APPLICATIONS

This application is a continuation-in-part of U.S. patent application Ser. No. 16/291,278 entitled "MODULAR PLATE AND CAGE ELEMENTS AND RELATED METHODS," filed Mar. 4, 2019, which in turn is a continuation of U.S. patent application Ser. No. 15/244,868 entitled "MODULAR PLATE AND CAGE ELEMENTS AND RELATED METHODS," filed Aug. 23, 2016, which claims priority to and benefit of U.S. Provisional Patent Application No. 62/270,141 entitled "MODULAR PLATE AND CAGE ELEMENTS AND RELATED METHODS," filed Dec. 21, 2015. This application also claims priority to and benefit of U.S. Provisional Patent Application No. 62/769,450 entitled "MODULAR FOOTPRINT CAGE SYSTEM," filed Nov. 19, 2018. The disclosures of each of these references are incorporated by reference herein in their entireties.

FIELD OF THE INVENTION

The present subject matter relates generally to devices for the fixation and support of vertebrae. In particular, the present subject matter relates to an implant device having adjustability.

BACKGROUND OF THE INVENTION

The spinal column of vertebrates provides support to bear weight and protection to the delicate spinal cord and spinal nerves. The spinal column includes a series of vertebrae stacked on top of each other. There are typically seven cervical (neck), twelve thoracic (chest), and five lumbar (low back) segments. Each vertebra has a cylindrical shaped vertebral body in the anterior portion of the spine with an arch of bone to the posterior, which covers the neural structures. Between each vertebral body is an intervertebral disk, a cartilaginous cushion to help absorb impact and dampen compressive forces on the spine. To the posterior, the laminar arch covers the neural structures of the spinal cord and nerves for protection. At the junction of the arch and anterior vertebral body are articulations to allow movement of the spine.

Various types of problems can affect the structure and function of the spinal column. These can be based on degenerative conditions of the intervertebral disk or the articulating joints, traumatic disruption of the disk, bone or ligaments supporting the spine, tumor or infection. In addition, congenital or acquired deformities can cause abnormal angulation or slippage of the spine. Anterior slippage (spondylolisthesis) of one vertebral body on another can cause compression of the spinal cord or nerves. Patients who suffer from one of more of these conditions often experience extreme and debilitating pain and can sustain permanent neurological damage if the conditions are not treated appropriately.

Alternatively, or in addition, there are several types of spinal curvature disorders. Examples of such spinal curvature disorders include, but need not be limited to, lordosis, kyphosis and scoliosis.

One technique of treating spinal disorders, in particular the degenerative, traumatic and/or congenital issues, is via surgical arthrodesis of the spine. This can be accomplished by removing the intervertebral disk and replacing it with implant(s) and/or bone and immobilizing the spine to allow the eventual fusion or growth of the bone across the disk space to connect the adjoining vertebral bodies together. The stabilization of the vertebra to allow fusion is often assisted by the surgically implanted device(s) to hold the vertebral bodies in proper alignment and allow the bone to heal, much like placing a cast on a fractured bone. Such techniques have been effectively used to treat the above-described conditions and in most cases are effective at reducing the patient's pain and preventing neurological loss of function.

The spinal curvature disorders and/or contour issues present on the surfaces of the vertebrae may present additional challenges. As such, there is need for further improvement, and the present subject matter is such improvement.

BRIEF SUMMARY OF THE INVENTION

The following presents a simplified summary of the subject matter in order to provide a basic understanding of some aspects of the subject matter. This summary is not an extensive overview of the subject matter. It is intended to neither identify key or critical elements of the subject matter nor delineate the scope of the subject matter. Its sole purpose is to present some concepts of the subject matter in a simplified form as a prelude to the more detailed description that is presented later.

In accordance with an aspect of the present subject matter, an implant device for the spine is provided. The implant device is for location between two adjacent vertebrae. The implant device includes: a first engagement surface configured to interface with a first of the two adjacent vertebrae; a second engagement member configured to interface with a second of the two adjacent vertebrae; and various modular components for independently adjusting a surface area or "footprint" of at least one of the first and/or second engagement surfaces.

In accordance with another aspect of the present subject matter, an implant device for the spine is provided. The implant device is for location between two adjacent vertebrae. The implant device includes: a first engagement member configured to interface with a lower surface of an upper vertebrae and an upper surface of an adjacent lower vertebrae; a second engagement member configured to interface with the lower surface of the upper vertebrae and the upper surface of the adjacent lower vertebrae; wherein at least a portion of the second engagement member is contained within at least a portion of the first engagement member.

In accordance with another aspect of the present subject matter, an implant device for the spine is provided. The implant device is for location between two adjacent vertebrae. The implant device includes: a first engagement member configured to interface with a lower surface of an upper vertebrae and an upper surface of an adjacent lower vertebrae, the first engagement member having an opening therein that extends from a lower implant surface to an upper implant surface; a second engagement member configured to interface with the lower surface of the upper vertebrae and the upper surface of the adjacent lower vertebra, the second engagement member sized to fit completely within the opening in the first engagement member.

In accordance with another aspect of the present subject matter, an implant device for the spine is provided. The implant device is for location between two adjacent vertebrae. The implant device includes: a first engagement member configured to interface with a lower surface of an upper vertebrae and an upper surface of an adjacent lower vertebrae, the first engagement member having an opening therein that extends from a lower implant surface to an upper implant surface; a second engagement member configured to interface with the lower surface of the upper vertebrae and the upper surface of the adjacent lower vertebra, the second engagement member nesting within and it contact with an inner surface of the first engagement member.

In accordance with another aspect of the present subject matter, a method for manufacturing an implant device as set for within any of the details described with the present application is provided.

In accordance with another aspect of the present subject matter, an implant device for the spine as set for within any of the details described with the present application is provided.

While embodiments and applications of the present subject matter have been shown and described, it would be apparent that other embodiments, applications and aspects are possible and are thus contemplated and are within the scope of this application.

The following description and the annexed drawings set forth in detail certain illustrative aspects of the subject matter. These aspects are indicative, however, of but a few of the various ways in which the principles of the subject matter may be employed and the present subject matter is intended to include all such aspects and their equivalents. Other objects, advantages and novel features of the subject matter will become apparent from the following detailed description of the subject matter when considered in conjunction with the drawings.

BRIEF DESCRIPTION OF THE SEVERAL VIEWS OF THE DRAWINGS

The foregoing and other features and advantages of the present subject matter will become apparent to those skilled in the art to which the present subject matter relates upon reading the following description with reference to the accompanying drawings. It is to be appreciated that two copies of the drawings are provided; one copy with notations therein for reference to the text and a second, clean copy that possibly provides better clarity.

FIG. 2B depicts a partially exploded perspective view of the nested interbody device of FIG. 2A;

FIG. 2C depicts a fully exploded perspective view of the nested interbody device of FIG. 2A;

FIGS. 3A through 3C depict perspective and exploded views of various alternative embodiments of a nested interbody device;

FIGS. 3D through 3F depict perspective views of various exemplary embodiments of nested interbody devices;

DETAILED DESCRIPTION OF THE INVENTION

Figure 1:
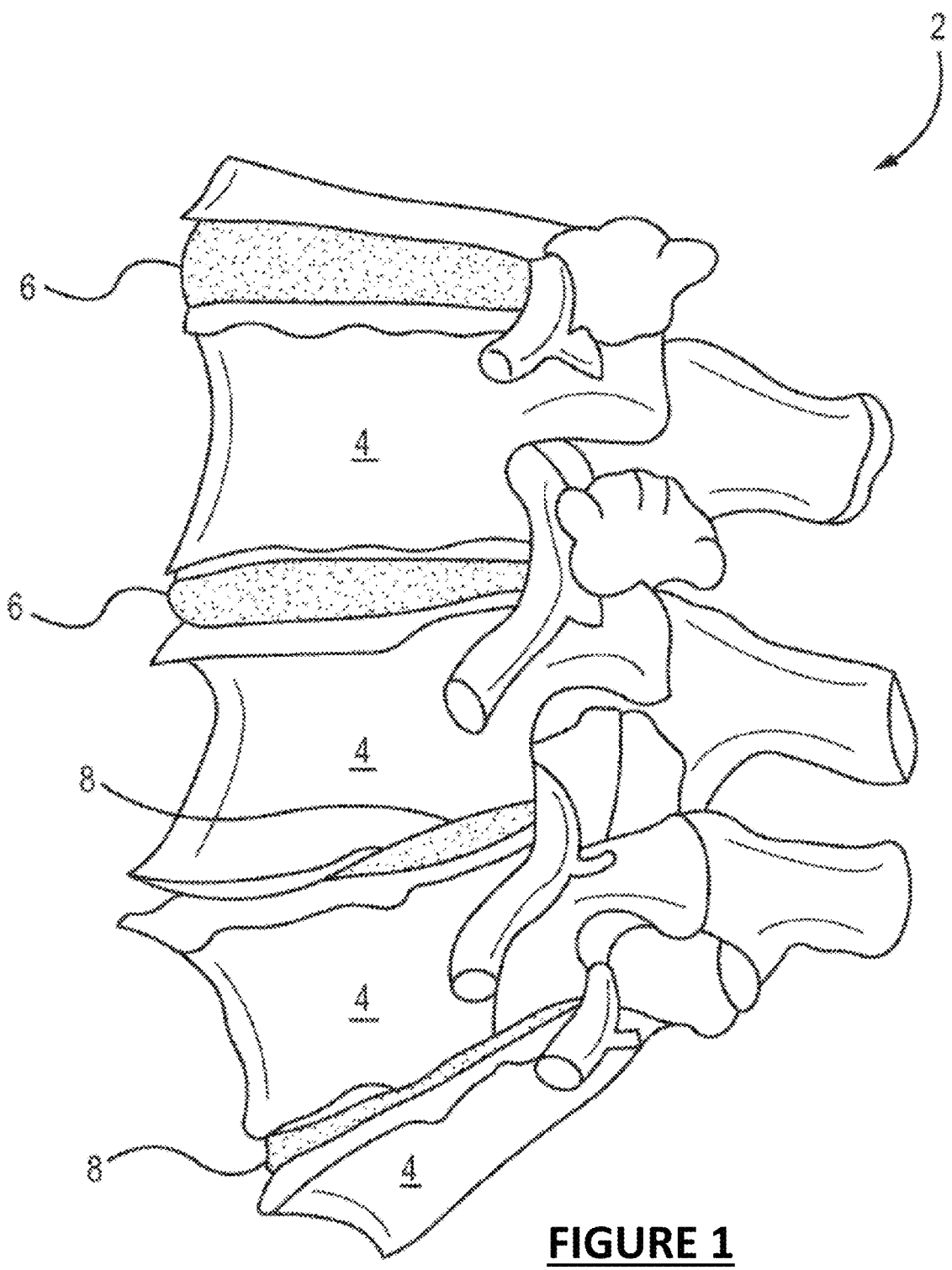
FIG. 1 depicts a portion of a patient's spinal column.

The present subject matter relates generally to devices for the fixation and support of vertebrae. In particular, the present subject matter relates to implant devices having adjustability. The spinal column of vertebrates provides support to bear weight and protection to the delicate spinal cord and spinal nerves. The spinal column includes a series of vertebrae stacked on top of each other. There are typically seven cervical (neck), twelve thoracic (chest), and five lumbar (low back) segments. Each vertebra has a cylindrical shaped vertebral body in the anterior portion of the spine with an arch of bone to the posterior, which covers the neural structures. Between each vertebral body is an intervertebral disk, a cartilaginous cushion to help absorb impact and dampen compressive forces on the spine. To the posterior, the laminar arch covers the neural structures of the spinal cord and nerves for protection. At the junction of the arch and anterior vertebral body are articulations to allow movement of the spine.

Various types of problems can affect the structure and function of the spinal column. These can be based on degenerative conditions of the intervertebral disk or the articulating joints, traumatic disruption of the disk, bone or ligaments supporting the spine, tumor or infection. In addition, congenital or acquired deformities can cause abnormal angulation or slippage of the spine. Anterior slippage (spondylolisthesis) of one vertebral body on another can cause compression of the spinal cord or nerves. Patients who suffer from one of more of these conditions often experience extreme and debilitating pain, and can sustain permanent neurological damage if the conditions are not treated appropriately.

Alternatively or in addition, there are several types of spinal curvature disorders. Examples of such spinal curvature disorders include, but need not be limited to, lordosis, kyphosis and scoliosis.

One technique of treating spinal disorders, in particular the degenerative, traumatic and/or congenital issues, is via surgical arthrodesis of the spine. This can be accomplished by removing the intervertebral disk and replacing it with implant(s) and/or bone and immobilizing the spine to allow the eventual fusion or growth of the bone across the disk space to connect the adjoining vertebral bodies together. The stabilization of the vertebra to allow fusion is often assisted by the surgically implanted device(s) to hold the vertebral bodies in proper alignment and allow the bone to heal, much like placing a cast on a fractured bone. Such techniques have been effectively used to treat the above-described conditions and in most cases are effective at reducing the patient's pain and preventing neurological loss of function.

The spinal curvature disorders and/or contour issues present on the surfaces of the vertebrae may present additional challenges. As such, there is need for further improvement. The present subject matter is such improvement. The present subject matter will now be described with reference to the drawings, wherein like reference numerals are used to refer to like elements throughout. It is to be appreciated that the various drawings are not necessarily drawn to scale from one figure to another nor inside a given figure, and in particular that the size of the components may be arbitrarily drawn for facilitating the understanding of the drawings. In the following description, for purposes of explanation, numerous specific details are set forth in order to provide a thorough understanding of the present subject matter. It may be evident, however, that the present subject matter can be practiced without these specific details. Additionally, other embodiments of the subject matter are possible and the subject matter is capable of being practiced and carried out in ways other than as described. The terminology and phraseology used in describing the subject matter is employed for the purpose of promoting an understanding of the subject matter and should not be taken as limiting.

The implant device and any portions or combination of portions thereof, such as those described and illustrated herein, can be constructed from radiopaque or radiolucent materials, other materials or combinations of such materials. Radiolucent materials can include, but are not limited to, polymers, carbon composites, fiber-reinforced polymers, plastics, combinations thereof and the like. One example of a radiolucent material that can be used with the present subject matter is PEEK-OPTIMA® polymer (commercially available from Invibio Inc., Greenville, S.C., USA). The PEEK-OPTIMA® polymer is a polyaromatic semicrystalline thermoplastic known generically as polyetheretherketone. The PEEK-OPTIMA® polymer is a biocompatible and inert material. Radiopaque materials are traditionally used to construct devices for use in the medical device industry. Radiopaque materials can include, but are not limited to, metal, aluminum, stainless steel, titanium, titanium alloys, cobalt chrome alloys, combinations thereof and the like.

Radiolucent materials can be utilized to facilitate radiographic evaluation of fusion material or vertebrae near an implant device. For example, radiolucent materials permit x-rays to pass through the implant device or components thereof so that developed x-ray pictures provide more visibility of the fusion material and vertebrae without significant interference, such as imaging artifacts, caused by the implant device. Radiolucent materials can enable clear visualization through imaging techniques such as x-ray and computer tomography (CT), whereas traditional radiopaque metallic or alloy materials can generate imaging artifacts or scatter that may prevent a comprehensive inspection of the surrounding tissue, vertebra and fusion material. In order to address the general disadvantage that some radiolucent materials lack the strength of radiopaque materials, design modifications may be required to provide adequate structural integrity and durability to the implant device. For example, the thickness of portions of the implant device subject to stress and strain can be increased in order to add support and structural integrity. Thicker or bulkier construction can mitigate the stresses of vertebral migration, subsidence and/or toggling of the implant components and/or bone fasteners that may cause the implant device to bend, crack or otherwise be damaged while in use.

Figure 2A:
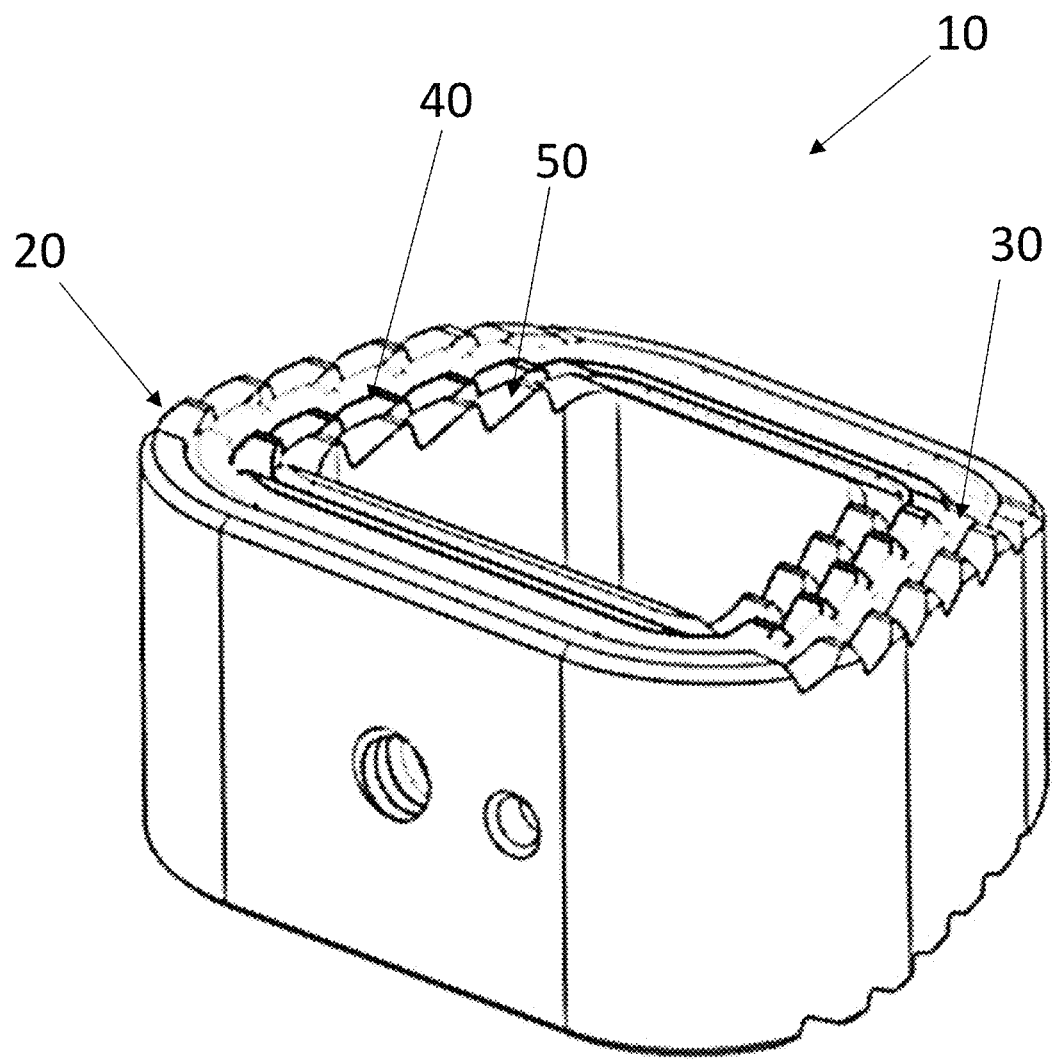
FIG. 2A is a perspective view of one exemplary embodiment of a nested interbody device.

Referring initially to FIG. 2A, an interbody implant device 10 that is presented is to be understood to be just one example embodiment. Other different embodiments are contemplated and are within the scope of this application. It is to be appreciated that the examples shown herein are suitable for insertion via a variety of surgical approaches, typically dependent upon implant size and/or shape and intervening patient anatomy. For example, some embodiment may be inserted anteriorly for treatment of cervical vertebral bodies. However, it is to be appreciated that other configurations for other insertion directions are contemplated.

The implant device 10 illustrated in FIG. 2A includes a first member 20, a second member 30, a third member 40 and a fourth member 50, with each of these members desirably configured to interface with a respective one (e.g., first and second) surface of two adjacent vertebrae. It is to be appreciated that each member may have a textured engagement surface that bears against the respective vertebra. The engagement surface may be textured in any suitable manner. The shown examples have teeth-like projections. However, it is contemplated that other texturing is possible. For example, the texturing may mimic the texturing of natural bone surface. Such could be accomplished via 3-D material building (e.g., 3-D printing). Metals, such as titanium and stainless steel, or other any other material could be employed for such 3-D material building.

In the disclosed embodiment, each member may include a plurality of engagement areas—such as wherein the engagement areas can be divided as desired into a plurality of areas such as an anterior wall section, a posterior wall section, a medial wall section, a lateral walls section and/or other sections. The areas can be via any divisions. For example, the engagement areas could be four corner areas. As another example, the engagement areas could be four areas defined to be fore, aft, left lateral and right lateral. It is to be appreciated that the choice of division into engagement areas need not be an overall limitation upon the subject matter.

In the disclosed embodiment, each of the members can desirably "nest" or otherwise stack or engage with adjacent members to create a "nested," nested or composite layered implant. In the embodiment disclosed in FIG. 2A, each of the members are of similar height but of steadily decreasing size (i.e., decreasing in width and thickness), which desirably allows each member to fit inside of the other members, such that member 30 fits within member 20, member 40 fits within member 30 and member 50 fits within member 40. In the disclosed embodiment, the individual members can be sized and configured to freely slide into each adjacent member, with a locking pin 80 (see FIG. 3A) or similar device that can be inserted into the members to secure the composite implant together. In alternative embodiments, there may be some amount of spacing and/or distance between adjacent surfaces of the members, if desired, of the various surfaces may fit more tightly together. In other embodiments, the members may include one of more engagement features such as detents, tabs, and/or tapers (i.e. a Morse taper extending downward in the center of each member) that engages the members to form a single implant when assembled.

In the embodiment of FIG. 3A, a central region 95 in the center of the composite implant can desirably accommodate a bone graft or other known material for inducing an arthrodesis between the adjacent vertebrae, including the use of solid bone graft plugs and/or morselized bone graft and/or paste material. If desired, one or more of the members may similarly be formed from a material that facilitates and/or induces bony growth through the member. In one exemplary embodiment, one member may comprise a wireframe, mesh or porous material that accommodates bone graft paste or other osteo-inductive materials.

Figure 3G:
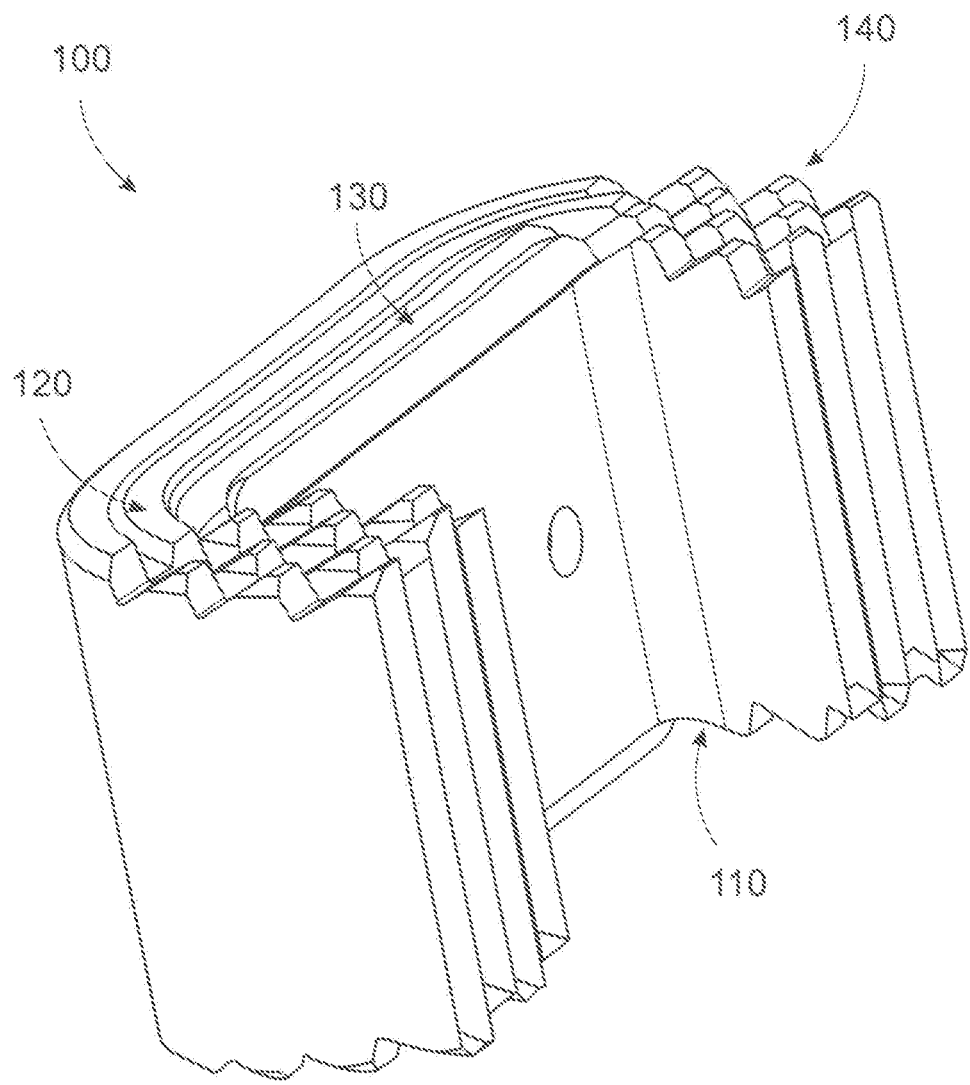
FIG. 3G depicts a perspective view of another alternative embodiment of a composite layered implant.

FIGS. 3B and 3G depict another alternative exemplary embodiment of a composite layered implant 100, where the individual members of the implant comprise open or "C-shaped" sections 110, 120, 130 and 140, which when assembled can be a secured by a locking pin 180. In this embodiment, each of the members can be aligned such that all of the C-shape members open towards a posterior side of the implant, if desired. Alternatively, the various members could be assembled in a variety of manners, including various arrangement where on or more of the members close off a portion of the C-shaped opening, if desired.

FIG. 3C depicts another alternative exemplary embodiment of a composite layered implant 200, where the members of the implant comprise various shaped members 210, 220, 230 and 240, which when assembled can be a secured by a locking pin (not shown) or other securing or locking arrangement. In this embodiment, each member desirably includes a complimentary inner and/or outer shape or shape features allowing the various members to be assembled together into a composite implant 200, but all of the members are not of identical shape (i.e., not just varying in size). For example, members 240, 230 and 220 can comprise c-C-shaped members, with member 210 comprising a ring or enclosed member.

FIGS. 3D through 3F illustrate various examples of a modular composite layered cage system 300, constructed according to the principles of the disclosure. In various embodiments, the shell-in-shell configuration of a modular cage system 300 can be used to minimize inventory of parts. The modular cage system 300 provides an adjustable footprint, wherein a closed loop geometry may be implemented (shown in FIG. 3A), an open loop geometry may be implemented (shown in FIG. 3B), or a hybrid closed-open loop geometry may be implemented (shown in FIGS. 3C and 3E).

Referring to FIGS. 3D and 3E, a modular cage system 300 may comprise a plurality of closed loop cage bodies 312, 314, 316, 318. Each of the cage bodies 312, 314, 316, 318, may have substantially the same shape and varying (e.g., increasing or decreasing) size (e.g., height, width, length, surface angle (e.g., angle of superior surface along posterior-anterior and/or lateral directions of cage body, and/or angle of inferior surface along posterior-anterior and/or lateral directions of cage body)), so that the cage bodies may be nested together to form a unitary configuration of the modular cage system 300, as seen in FIG. 3E, by nesting one inside another. One or more of the cage bodies 312, 314, 316, 318 may have a different shape and/or size than the other cage bodies. The cage bodies may be selected and nested together to form a cage system 300 that matches the size, shape, contours, etc. of the adjacent vertebrae surfaces. Each of the cage bodies 312, 314, 316, 318 may be made of a single material or combination of various materials for, for example, radio-opaque and/or strength effects. The cage bodies 312, 314, 316, 318 may be made of the same or different materials. The modular cage system 300 may include, for example, two, three, four, or more cage bodies.

The cage bodies 312, 314, 316, 318 each have a graft chamber GC, whose dimensions and position may be varied by varying the thicknesses and/or shapes of the walls of the respective cage body. For instance, by making one of the four walls of the cage body 312 much thicker than the other three walls, the center of the graft chamber GC may be shifted away from the thicker wall. Further, by altering the inner contours of the walls of a cage body, the shape of the graft chamber GC may be selectively determined. The outer contours of the walls of one or more of the cage bodies 312, 314, 316, 318 may be varied to form cage bodies based on the particular anatomy of a patient.

Figure 9A:
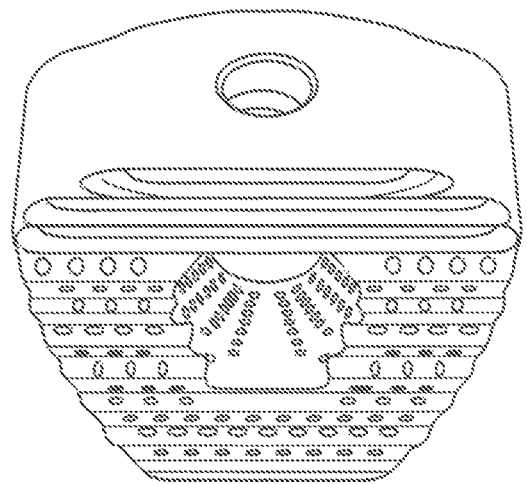
FIGS. 9A through 9E depicts various component materials for modular members of nested interbody devices.
Figure 9B:
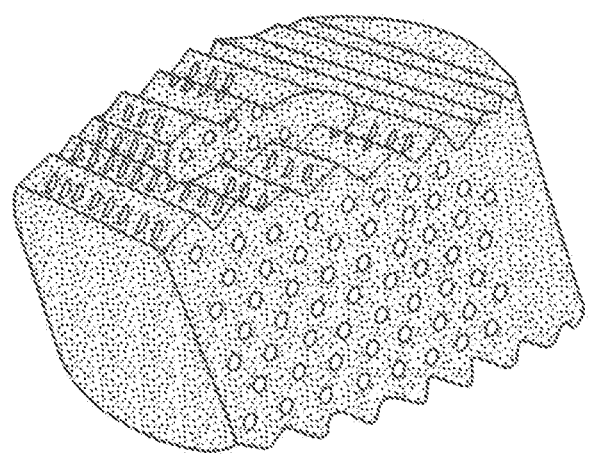
Figure 9C:
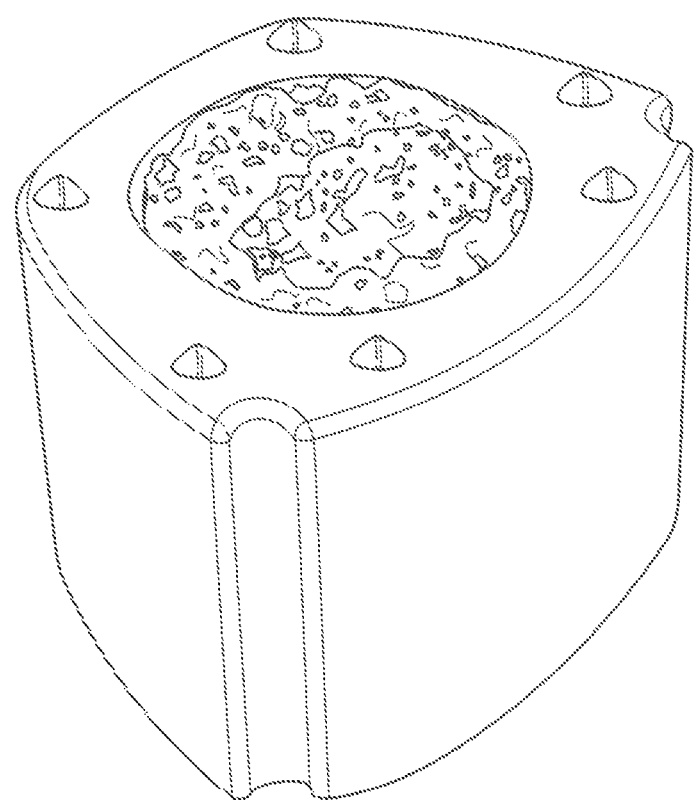
Figure 9D:
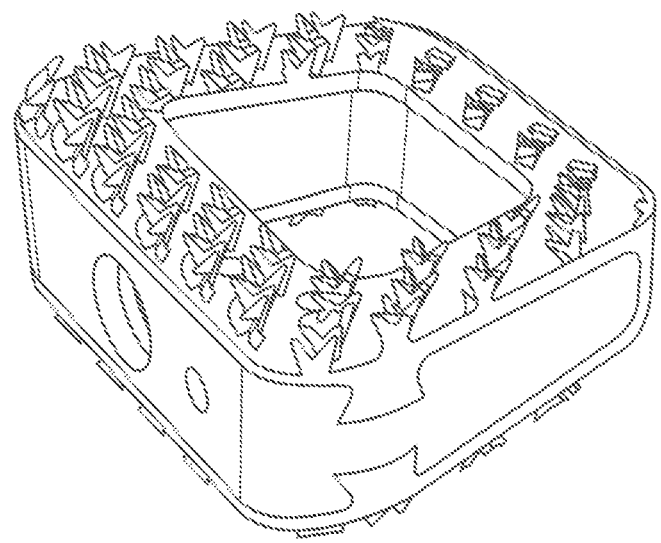
Figure 9E:
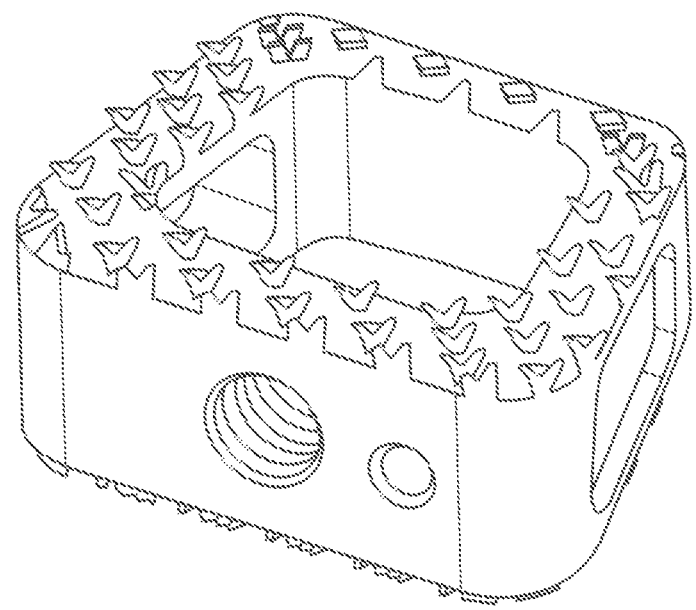

Referring to FIG. 3F, a hybrid modular cage system 319 comprises a pair of open loop cage bodies 315, 317 nested in the closed loop cage body 318. The open loop cage bodies 315, 317 may each be formed with three walls, as seen in the illustration. Each of the cage bodies 315, 317, may have substantially the same shape and increasing (or decreasing) size, so that the cage bodies may be nested together to form a unitary configuration of the modular cage system 319, as seen in FIG. 9C, by nesting one inside another. The cage body 318 may have substantially the same (or different) shape as the open loop cage body 315 and/or 317, so as to receive and hold each of the cage bodies 315, 317 in the graft chamber GC of the cage body 318. One or more of the cage bodies 315, 317, 318 may have a different shape than the other cage bodies. Each of the cage bodies 315, 317, 318 may be made of a single material or combination of various materials for, for example, radio-opaque and/or strength effects. The cage bodies 315, 317, 318 may be made of the same or different materials.

In various embodiments, one or more of the cage bodies 315, 317 may be nested in the cage body 318 to modify the dimensions, position and/or shape of the graft chamber GC in the cage body 318. By selecting wall dimensions and shapes of each of the cage bodies 315, 317, and nesting the cage bodies 315, 317 in a predetermined direction, the dimensions, position and/or shape of the graft chamber GC may be selectively determined. The predetermined direction may comprise, for example, the open end of the cage body 315 facing in the same or a different direction than the open end of the cage body 317. As seen in FIG. 3F, the open ends of the cage bodies 315, 317 may be positioned in the same direction, so as to position the center of the graft chamber GC toward the open end of the cage bodies 315, 317, when nested in the configuration seen in FIG. 3F. By making one of the walls of a cage body much thicker than the other three walls, the center of the graft chamber GC may be shifted away from the thicker wall. Further, by altering the inner contours of the walls of a cage body, the shape of the graft chamber GC may be selectively determined. The outer contours of the walls of one or more of the cage bodies 315, 317, 318 may be varied to form cage bodies based on the particular anatomy of a patient.

In various embodiments, the individual members of a composite layered implant may comprise the same material or may comprise differing materials, with each of the members having a variety of shapes and/or purposes. For example, a composite layered implant may comprise an outer member of titanium or other load-bearing material, with one or more inner members comprising an osteo-inductive and/or osteo-conductive material such as Silicon Nitride. If desired, an intermediate layer of a composite layered implant may comprise a non-loading bearing material such as morselized bone graft and/or granular or powdered silicone nitride, with load bearing members such as titanium or PEEK positioned inside and/or outside of the non-load bearing members. The disclosed modular implants and/or "cage" structures can also allow for various combinations of materials to be integrated and implanted in a single cage. For example, an outer layer if silicon nitride to promote bony ingrowth may "cover" an inner layer of titanium that provides strength and/or support for the implant. In various embodiments, a composite implant incorporating 4 layered members may include 4 differing materials in the implant walls, with an optional amount of bone graft and/or other material located within the central opening or bore of the implant. A variety of such component materials could be employed, including metal, plastics and/or ceramics, including (but not limited to) PEEK, titanium, chrome cobalt, allograft, autograft or xenograft bone or other materials, solid Silicon Nitride (see FIG. 9A) and/or porous Silicon Nitride, as well as other materials well known in the art (see FIGS. 9A through 9E).

In various embodiments, a composite layered implant such as described herein may comprise a plurality of modular members or layers, with multiple nested layers being added and/or removed from the implant to accommodate an individual patient's anatomy and/or the desires of the surgeon. In many cases, a composite layered implant may be assembled at a back-table location during a surgical procedure to desirably achieve a largest and/or optimal footprint for placement between two adjacent vertebrae. By removing and/or adding various layers to the device, a composite layered implant can be created and/or assembled to achieve a desired clinical effect.

Figure 4A:
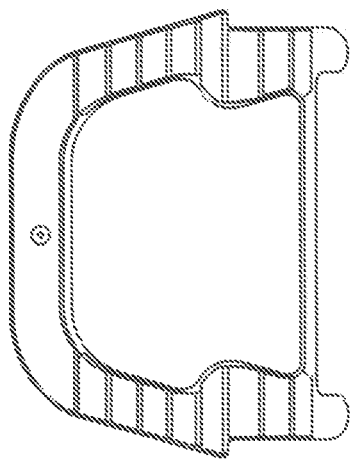
FIGS. 4A and 4B depict top plan views of individual small, medium and large sized members which can form part of a surgical kit for assembling composite layered implants.
Figure 4A:
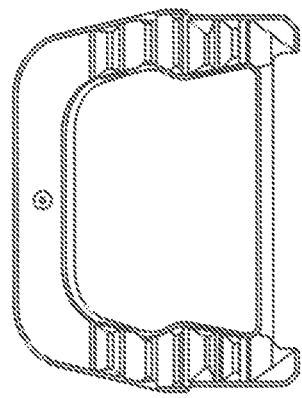
Figure 4A:
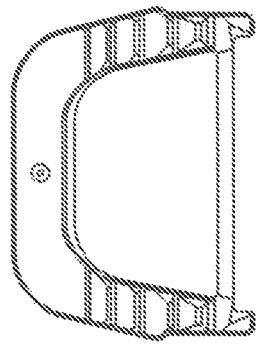
Figure 4B:
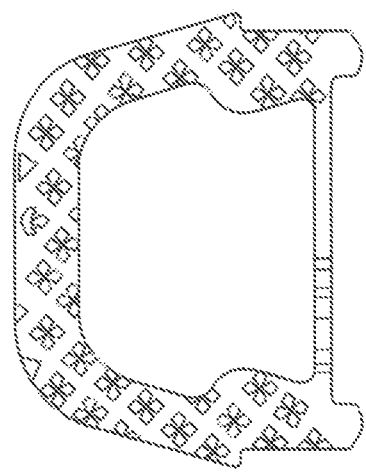
Figure 4B:
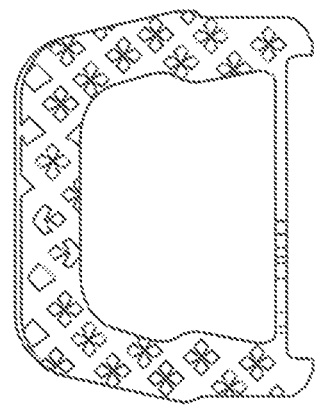
Figure 4B:
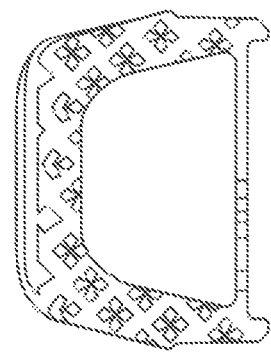

FIGS. 4A and 4B depict individual small, medium and/or large sized members which can form part of a surgical kit for assembling composite layered implants. In FIG. 4A, one or more of the members can include a ribbed upper and/or lower surface for engaging with the corresponding endplate surfaces of the adjacent vertebra, while in FIG. 4B one of the members are shown as having textured upper and/or lower surfaces such as a textured TiCro™ surface treatment technology (commercially available from CTL Amedica of Addison, Tex., USA), which allows for immediate fixation and/or long term bony ingrowth with the corresponding endplate surfaces of the adjacent vertebra. If desired, a composite layered implant may include different component members having a variety of surface treatments known in the art, including those disclosed herein.

Figure 4C:
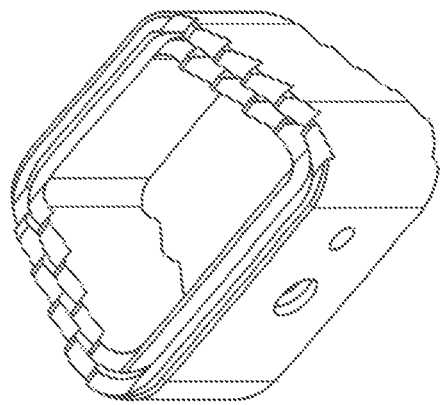
FIG. 4C depicts different sized composite layered implants in large, intermediate and small sizes that employ some similar sized and shaped component members.
Figure 4C:
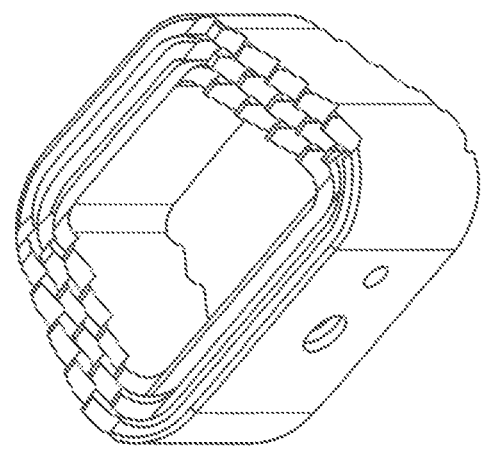
Figure 4C:
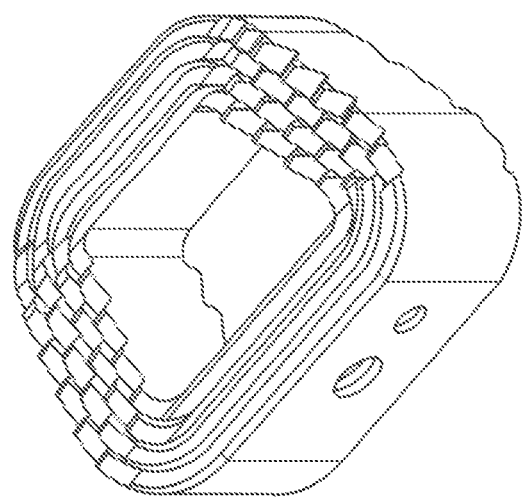

FIG. 4C depicts three different sized composite layered implants, such as a large, intermediate and small sized implants, wherein each of the implant sizes includes some identical components (i.e., the largest implant includes identical components to the smaller implants). A kit containing a variety of such implants can be provided to a physician or medical practitioner to allow the creation of a variety of sized and/or shaped implants, including implants useful for different sized patients, using a single set of components (i.e., modular members) that can be assembled into different sizes and/or shapes. Desirably, composite layered and/or modular nesting implants such as those described herein can greatly reduce required inventory for an implant kit, as the modular components allow for a wide variety of sizes for outer and/or inner layers. In various embodiments, optimal sizes for various implants may depend upon vertebral anatomy, surgical procedures and/or access, available implant "real estate" and/or placement, as well as desired amount of bone graft and/or other materials that may be placed within and/or integrated into the implant components.

Figure 5A:
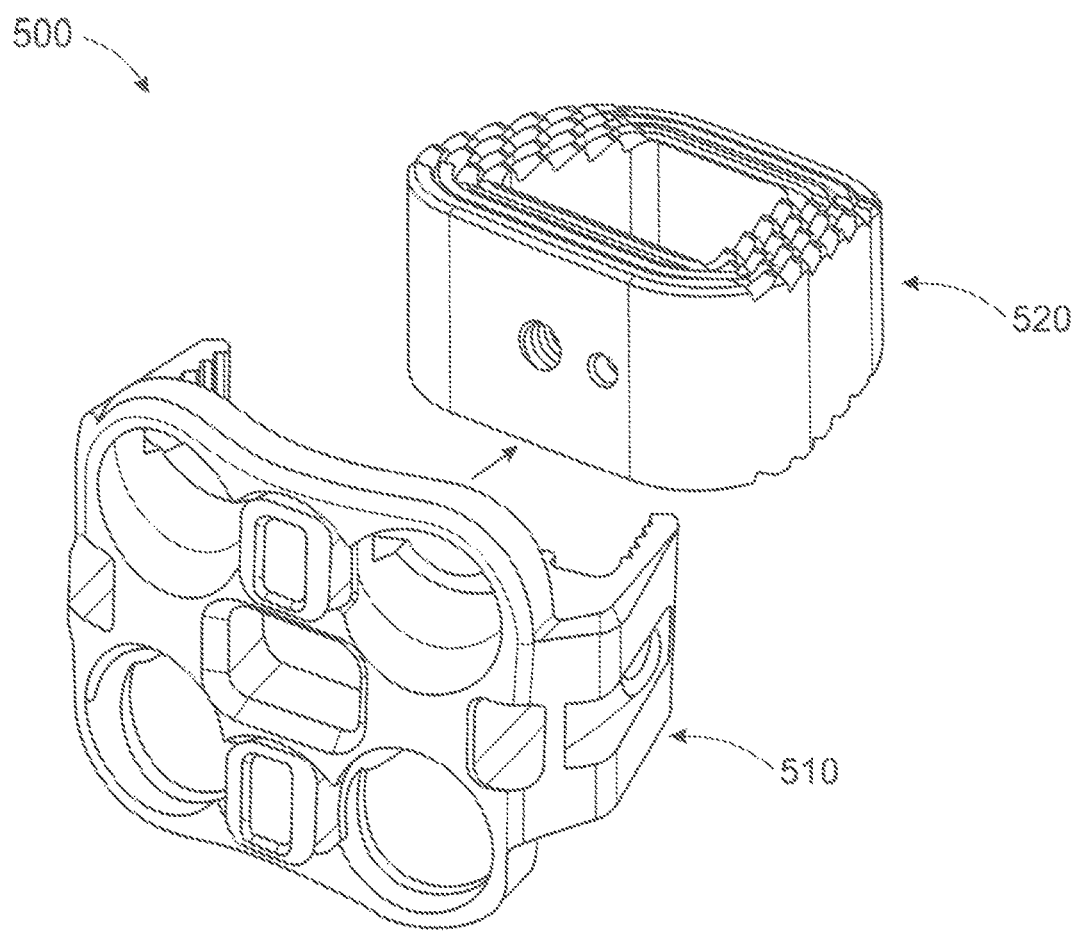
FIGS. 5A through 5F depict various views of alternative embodiments of interbody systems that include various interbody devices and one embodiment of an attachable composite layered implant or interbody cage.
Figure 5B:
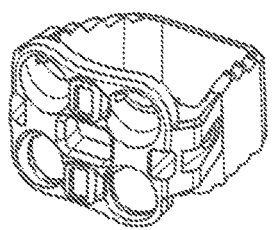
Figure 5C:
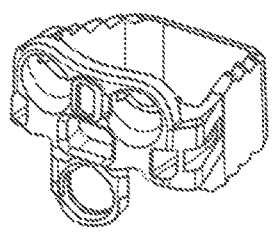
Figure 5D:
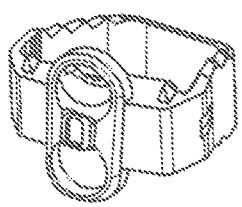
Figure 5E:
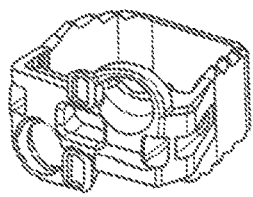
Figure 5F:
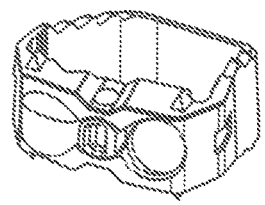
Figure 6A:
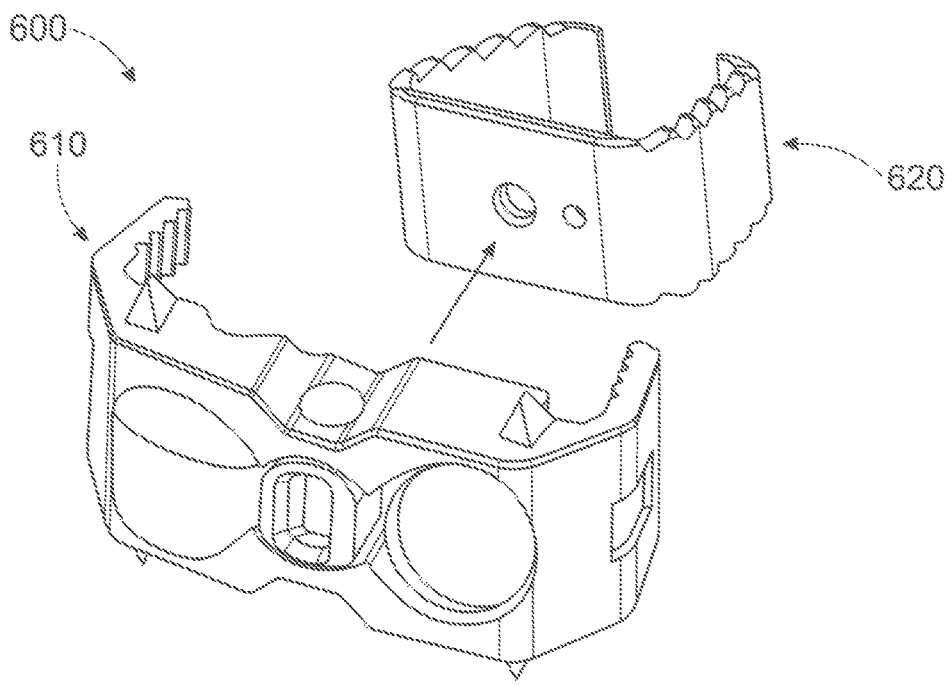
FIGS. 6A through 6F depict various views of other alternative embodiments of interbody systems that include various interbody devices and one embodiment of an attachable composite layered implant or interbody cage.
Figure 6B:
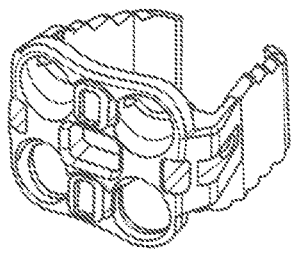
Figure 6C:
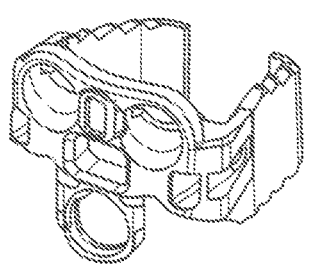
Figure 6D:
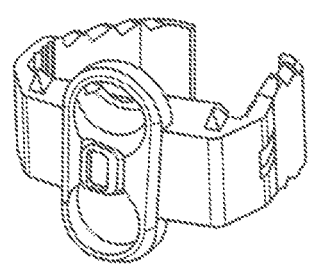
Figure 6E:
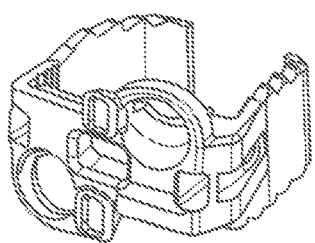
Figure 6F:
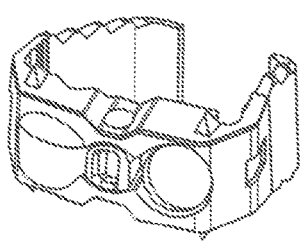

FIGS. 5A through 5F depict exemplary embodiments of an interbody system 500 that includes an interbody device 510 and an attachable composite layered implant or interbody cage 520. The interbody system 500 may be formed as a single structure (not shown), or it may be assembled from two or more pieces such as shown in FIG. 5A.

For instance, the interbody system 500 may be assembled by attaching the interbody device 510 to the cage 520. In this regard, the interbody device 510 may be positioned so that channels or other guiding features may be aligned with corresponding plate guides on the cage, or other known engagement features, if desired. Once assembled, the interbody system may be implanted between the vertebral bodies and secured to one or more of the vertebral bodies using fixation devices such as bone screws (not shown).

FIGS. 6A through 6F depict another exemplary embodiments of an interbody system 600 that includes various interbody devices 610 and an attachable composite layered implant or interbody cage 620.

Figure 7A:
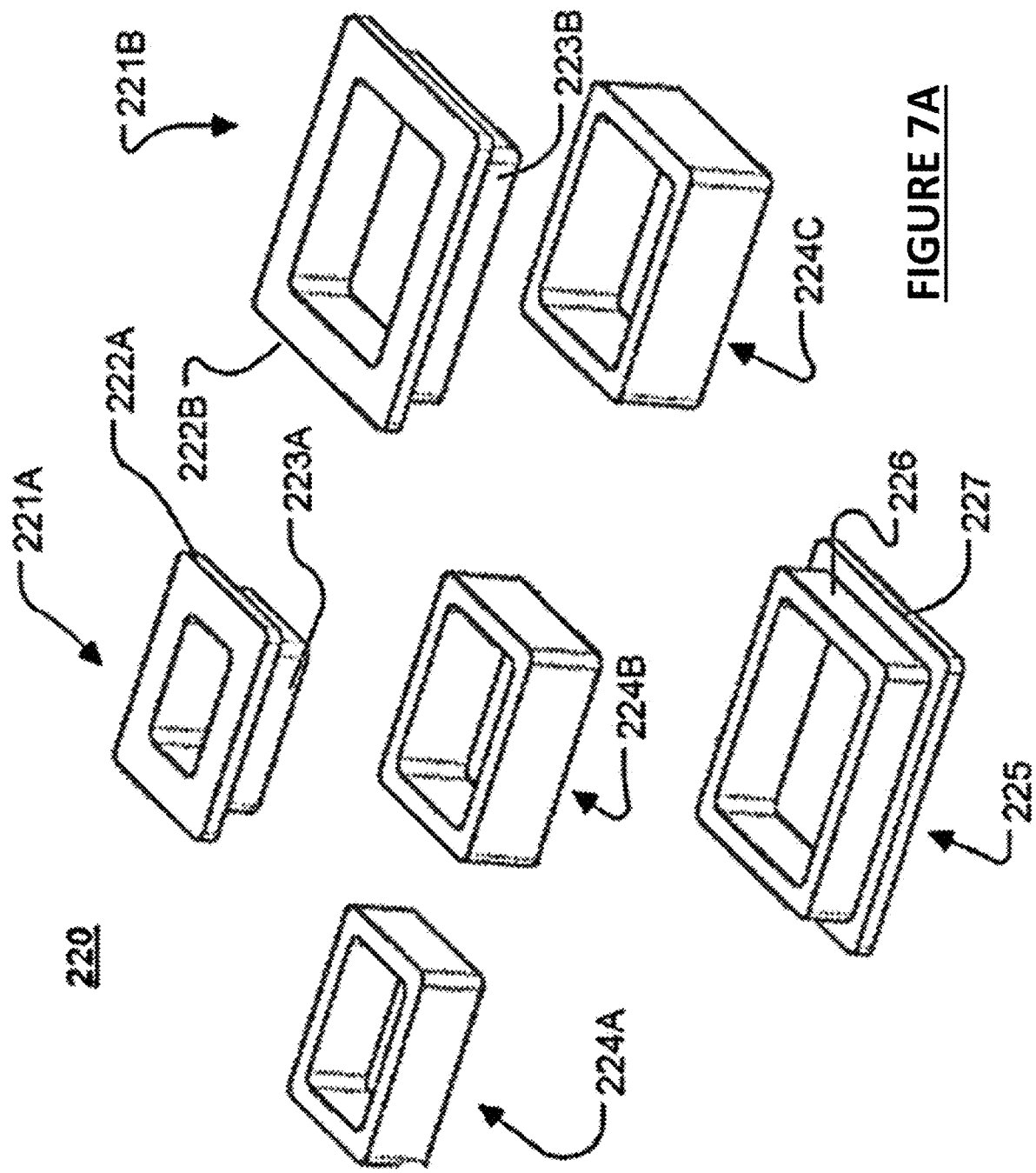
FIGS. 7A through 7H depict various views of alternative embodiments of modular cage systems incorporating one or more modular end caps for altering vertebral angulation.
Figure 7C:
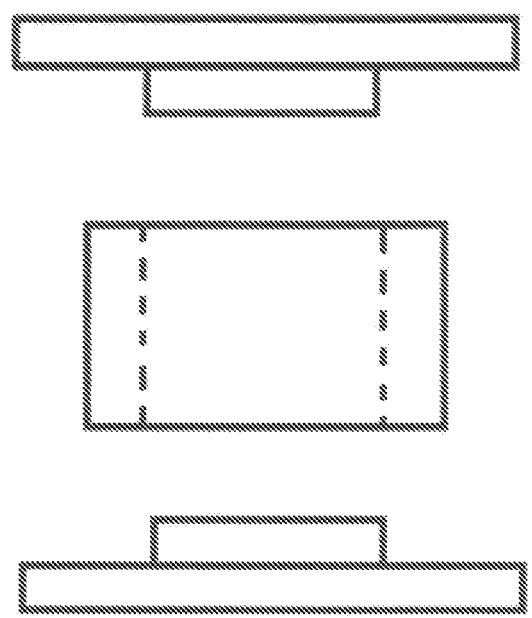

FIGS. 7A through 7H depict various views exemplary embodiments of modular cage systems having one or more modular end caps for altering vertebral angulation. The modular cage system 220 may comprise a plurality of closed loop cage bodies 224A, 224B, 224C. The modular cage system 220 may, instead, include all open loop cage bodies (not shown), or a hybrid system of open and closed loop cage bodies (not shown). The modular cage system 220 may further include one or more end caps 221A, 221B, 225. Each of the cage bodies 224A, 224B, 224C, may have substantially the same shape with varying (e.g., increasing or decreasing) size (e.g., height, width, length, surface angle (e.g., angle of superior surface along posterior-anterior and/or lateral directions of cage body, and/or angle of inferior surface along posterior-anterior and/or lateral directions of cage body)), as seen in FIG. 7A, so that the cage bodies 224A, 224B, 224C may be interchangeably used with one or more of the end caps 221A, 221B, 225. One or more of the cage bodies 224A, 224B, 224C may have a different shape than the other cage bodies. Each of the cage bodies 224A, 224B, 224C and/or the end caps 221A, 221B, 225 may be made of a single material or combination of various materials for, for example, radio-opaque and/or strength effects. The cage bodies 224A, 224B, 224C and/or the end caps 221A, 221B, 225 may be made of the same or different materials.

The cage bodies 224A, 224B, 224C may have any shape that may be implemented in an application between vertebral bodies, as will be understood by those skilled in the art. For instance, the cage bodies 224A, 224B, 224C may have a trapezoidal shape, with the side walls tapered inward in the posterior direction (not shown), or the shape of the cage bodies 224A, 224B, 224C may be a square, rectangular, elliptical, circular, semicircular, or the like. The end caps 221A, 221B, 225 may have a shape that matches the shape of the cage bodies 224A, 224B, 224C.

As seen in FIGS. 7A, the end caps 221A, 221B, 225 may each include an insert portion 223A, 223B, 226, respectively, and/or a rim portion 222A, 222B, 227, respectively. For instance, referring to the end cap 221A with the understanding that the description equally applies to the end caps 221B and 225, the end cap 221A includes an insert portion 223A that may be inserted into the opening of the cage body 224A (or 224B or 224C), and a rim portion 222A that may function as a stop and/or cap for the cage body 224A (or 224B or 224C). The thickness, size and/or shape of the wall portions that form the insert portion 223A may be predetermined so as to selectively determine the position, shape, and/or size of the graft chamber in the cage body 224A (or 224B or 224C). For instance, the walls of the insert portion 223A may be varied in terms of size and shape, including, for example, height, width, length, surface angles, so as to determine the shape, position and size of the graft chamber in the cage body 224A (or 224B or 224C) when the end cap 221A is attached to the cage body 224A.

Similarly, the thickness, size and/or shape of the rim portion 222A may be varied to, for example, match anatomical requirements for particular applications of the cage system. For instance, the height of the walls that form the rim portion 222A may be decreased (or increased) in the posterior (or anterior) direction, so as to provide better fit in vertebral interbody applications. The rim portion 222A may be configured to contact and engage a vertebral body. In this regard, the surface of the rim portion 222A may be contoured to match the shape of the vertebral body. The surface may include bone interface members that may be configured to aggressively grip against the bony surface of the adjacent vertebral body.

Figure 7B:
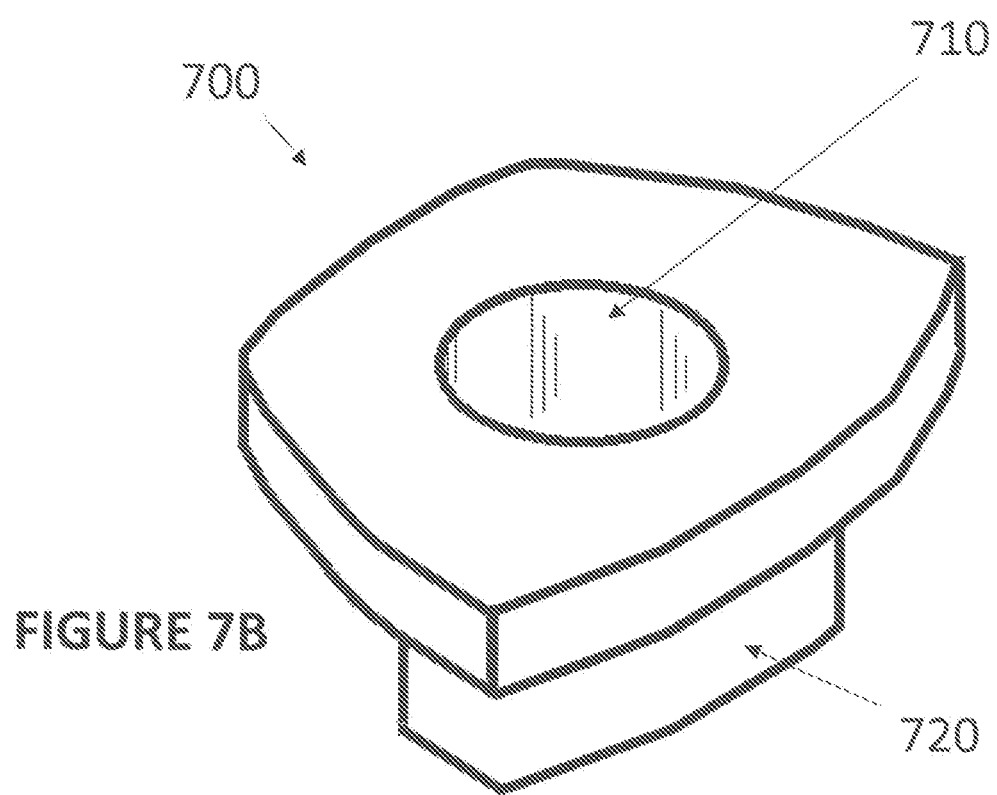
Figure 7D:
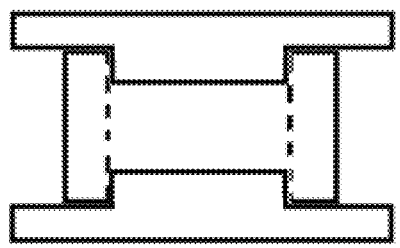
Figure 7E:
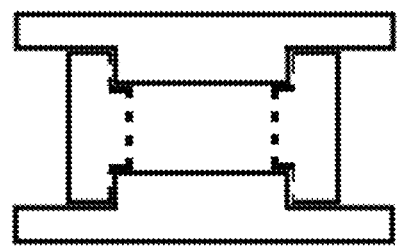
Figure 7F:
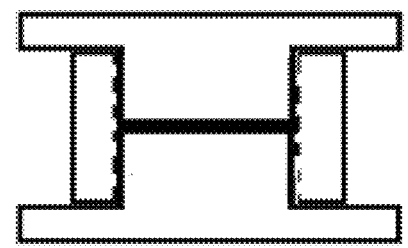

As best seen in FIG. 7B, an exemplary end cap 700 can include an insert portion 720 and a central opening 710 which can extend from an outer surface of the cap 700 through the insert portion 720 and which may be desirably in fluid communication with the graft chamber of the cage body (not shown). In some embodiments, the insert portion 720 of the end cap may be smaller than the thickness of the cage body (see FIG. 7D), while in other embodiments the insert portion 720 of the end cap may be of varying lengths, and in some embodiments the insert portion 720 may be sufficiently long to engage with a lip formed on an inner wall surface of the graft chamber (see FIG. 7E), while in still other embodiments a surface of the end cap may contact an opposing surface of an opposing end cap (i.e., extending from the bottom surface of the cage body)—(see FIG. 7F), or upper and lower surfaces of a composite member positioned within the central opening.

Figure 7G:
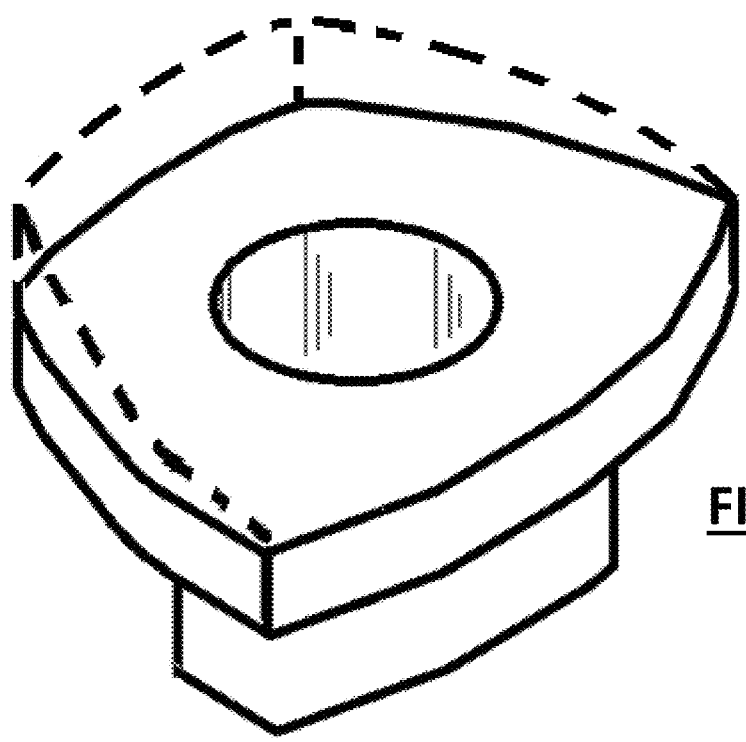
Figure 7H:
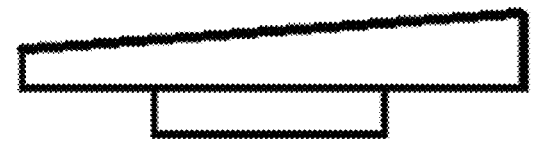
Figure 7H:
Figure 7H:
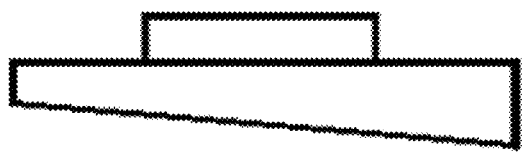

FIGS. 7G and 7H depict end caps having a slanted or angled upper surface, which can desirably be contoured to match the shape of the vertebral body and/or selected to achieve a desired "correction" to the angular relationship between the adjacent vertebral bodies. Such an angulation can be formed in any direction, including medial, lateral, anterior, posterior and/or various combinations thereof, including the employment of concave, convex and/or complex straight and/or curved planar surfaces. In some embodiments, a plurality of end caps of different shapes and/or sizes can be provided in a kit, so as to allow a medical practitioner to create a desired implant during a surgical procedure once the vertebral surfaces have been accessed and/or prepared. If desired, one or more surfaces of an end cap may include bone interface members that may be configured to aggressively grip against the bony surface of the adjacent vertebral body.

In various embodiments, a modular implant system could include upper and/or lower endcaps that could integrate with various system components, including a modular composite cage, to alter the size, shape, footprint and/or tilt of the implant. The endcaps could individually fit in one side and/or end of the cage, and/or into both sides and/or ends of the cage, and the system could include a variety of locking features for securing the endcap(s) to each other and/or to the cage (and/or could secure the entire modular implant together, if desired).

Figure 8C:
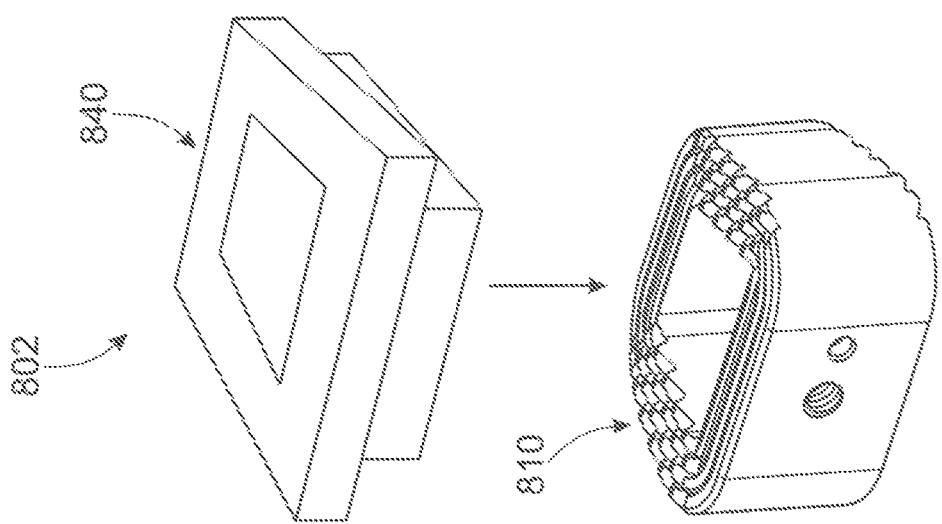
FIGS. 8A through 8C depict various views of alternative embodiments of modular cage systems modular composite cage components and/or end caps.
Figure 8B:
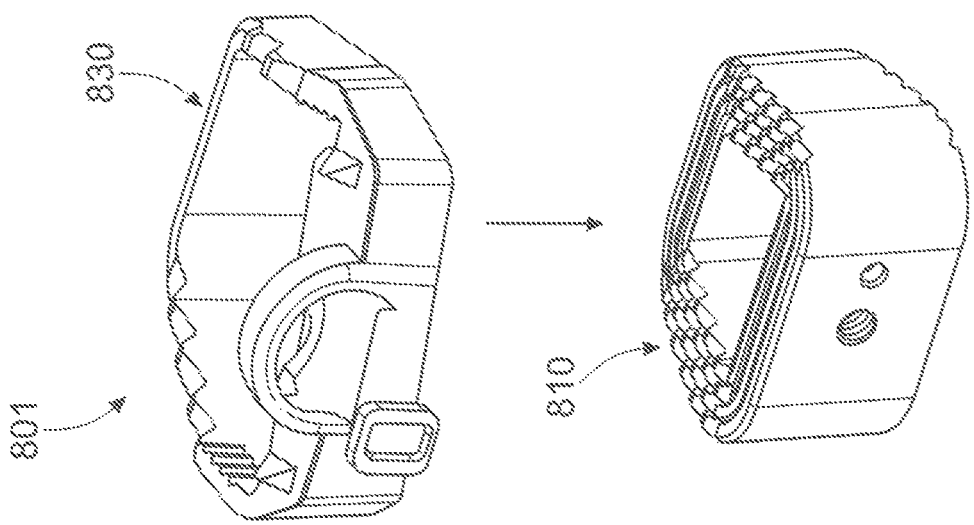
Figure 8A:
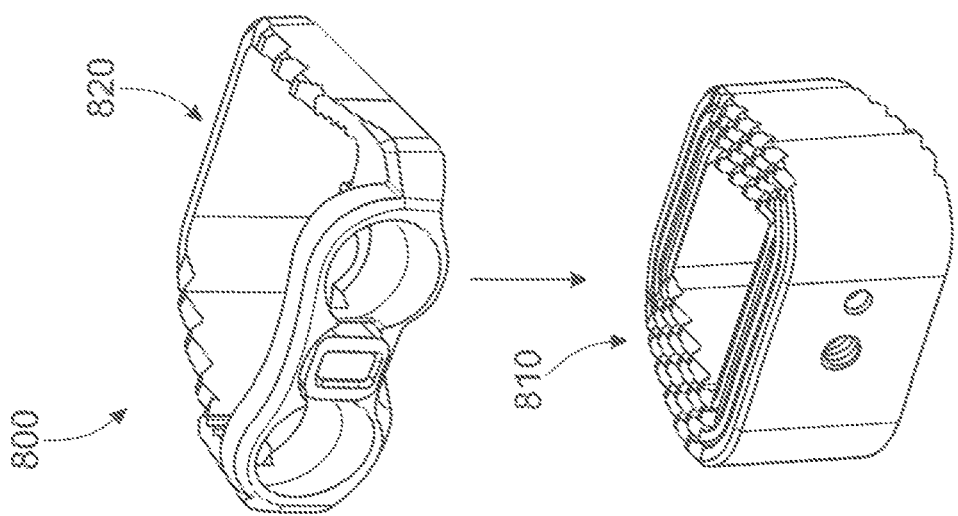

FIGS. 8A through 8C depict various exemplary embodiments of modular cage systems 800, 801 and 802, each system incorporating a composite cage 810 and various alternative interbody devices 820 and 830 or an end cap 840. The various components of these systems could optionally be provided in kit form, with a medical practitioner having the option to select an appropriately sized and/or shaped composite cage, and then attach a desired interbody device or end cap necessary to address a desired surgical situation.

Figure 10A:
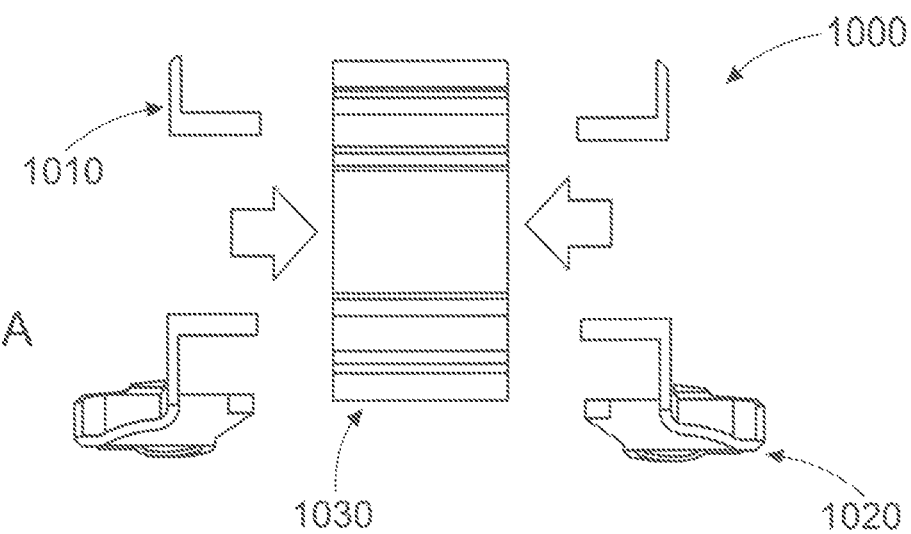
FIGS. 10A through 10C depict views of another exemplary embodiment of a modular cage system with a two-piece modular endplate configuration.
Figure 10B:
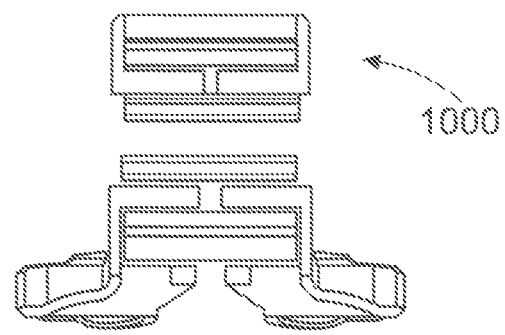
Figure 10C:
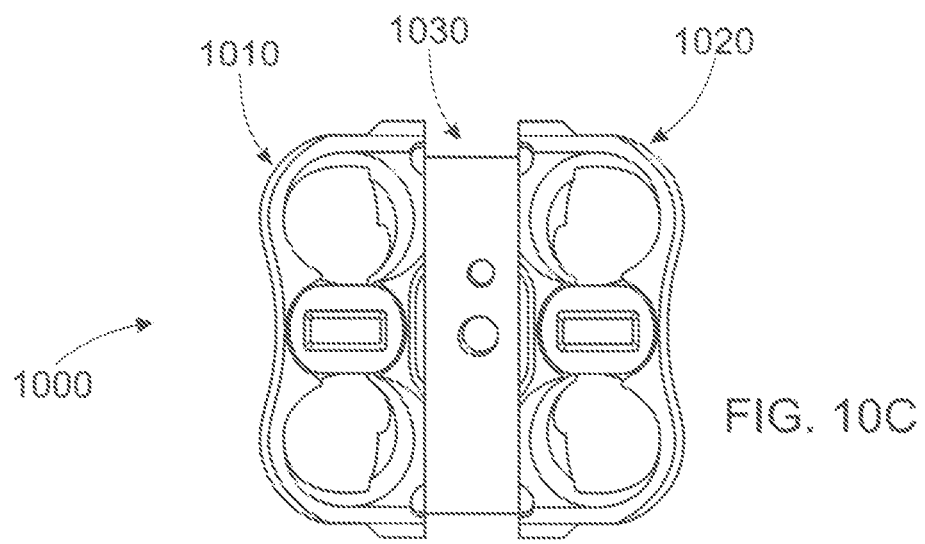

FIGS. 10A through 10C depicts views of another exemplary embodiment of a modular cage system 1000 with a two-piece modular endplate configuration. In this embodiment, an upper endplate module 1010 and a separate lower endplate module 1020 can be attached to a composite cage 1020. In a manner similar to the various embodiments described herein, the upper and lower endplate modules 1010 and 1020 can be provided in a kit containing upper and/or lower modules of varying shapes and/or sizes to assemble a desired implant. In addition, in some embodiments the upper and lower modules can be reversible and/or interchangeable, such that a required inventory of such modules in a kit can be further reduced, as desired.

Note that, in various alternative embodiments, variations in the position and/or relationships between the various figures and/or modular components are contemplated, such that different relative positions of the various modules and/or component parts, depending upon specific module design and/or interchangeability, may be possible. In other words, different relative adjustment positions of the various components may be accomplished via adjustment in separation and/or surface angulation of one of more of the components to achieve a variety of resulting implant shapes and/or sizes, thereby accommodating virtually any expected anatomical variation. For example, variation of the thicknesses and/or separation distance between the end caps (i.e., optionally without altering the angulation of the end cap surfaces) can desirably cause an increase or decrease in the size or "height" of the implant, due to changes in the z-axis positioning of the implant components which engage the adjacent vertebrae. Concurrently, alterations in the "tilt angle" or angulation of one or both of the surfaces of the end caps or other components in the medial-lateral (i.e., rotation about a y-axis) and/or anterior-posterior (i.e., rotation about an x-axis) axes of the implant will allow the implant to accommodate a wide variety of natural and/or surgically altered surfaces of the spine. Moreover, various complex combinations (at various amounts) of comparative lateral (e.g., left-right) tilt and fore-aft (e.g., anterior-posterior) tilt can be accomplished, with or without concurrent adjustments in the height of the implant. In various embodiments, each respective surface of a composite implant, and end cap or other components (e.g., each corner) of a given component can have a different adjusted distance as compared to the other respective engagement areas (e.g., other corners), if desired.

The various embodiments of a composite modular implant device disclosed herein can be configured to interact with two bone vertebrae of a spine. The spine may have any of several types of spinal curvature disorders which are sought to be treated. Examples of such spinal curvature disorders include, but need not be limited to, lordosis, kyphosis, scoliosis and/or low and/or high velocity fractures, among other pathologies.

In various exemplary scenarios, the implant devices disclosed herein can be utilized to fix and/or secure adjacent vertebrae that have had cartilaginous disc between the vertebrae replaced with fusion material that promotes the fusion of the vertebrae, such as a graft of bone tissue. Also, such can be accomplished even when dealing with a spinal curvature disorder (e.g., lordosis, kyphosis and scoliosis).

Of course, method(s) for manufacturing the implant device and implanting the device into a spine are contemplated and are part of the scope of the present application.

While embodiments and applications of the present subject matter have been shown and described, it would be apparent to those skilled in the art that many more modifications are possible without departing from the inventive concepts herein. The subject matter, therefore, is not to be restricted except in the spirit of the appended claims.

All references, including publications, patent applications, and patents, cited herein are hereby incorporated by reference to the same extent as if each reference were individually and specifically indicated to be incorporated by reference and were set forth in its entirety herein.

The various headings and titles used herein are for the convenience of the reader, and should not be construed to limit or constrain any of the features or disclosures thereunder to a specific embodiment or embodiments. It should be understood that various exemplary embodiments could incorporate numerous combinations of the various advantages and/or features described, all manner of combinations of which are contemplated and expressly incorporated hereunder.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., i.e., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A modular implant device for the spine, the modular implant device for placement between two adjacent vertebrae, comprising:
   a first member sized to span at least a portion of a distance between the two adjacent vertebrae, the first member including a first body having a first upper surface and a first lower surface and a first opening formed through the body which extends from the first upper surface to the first lower surface, the first opening having a first height;
   a second member sized to span at least a portion of a distance between the two adjacent vertebrae, the second member including a second body having a second upper surface and a second lower surface and a second height, the second height being less than the first height, the second body being sized and configured to fit fully within the first opening;
   a first end cap having a first insert portion that fits within the first opening and a first rim portion which extends upwards from the insert portion, wherein the first rim portion further includes a first engagement surface for engaging an endplate portion of a first vertebral body of the two adjacent vertebrae, wherein when the second body is positioned fully within the first opening and the first insert portion of the first end cap is positioned within the first opening, the second upper surface is substantially in contact with at least a portion of a lower surface of the first insert portion, and
   a second end cap having a second insert portion that fits within the first opening and a second rim portion which extends downwards from the second insert portion, the second rim portion including a second engagement surface for engaging an endplate portion of a second vertebral body of the two adjacent vertebrae, wherein when the second body is positioned completely within the first opening and the second insert portion is positioned within the first opening, the second lower surface of the second body is substantially in contact with at least a portion of an upper surface of the second insert portion.

2. The modular implant device of claim 1, wherein a cross-sectional dimension of the first rim portion is greater than a cross-sectional dimension of the first member.

3. The modular implant device of claim 1, wherein the first member comprises a first material and the second member comprises a second material, wherein the first and second materials are the same material.

4. The modular implant device of claim 1, wherein the first member comprises a first material and the second member comprises a second material, wherein the first and second materials are different materials.

5. The modular implant device of claim 1, wherein at least one of the first and second members comprise silicon nitride.

6. The modular implant device of claim 1, wherein at least a portion of the modular implant device comprises silicon nitride.

7. The modular implant device of claim 1, wherein the first and second engagement surfaces are substantially parallel.

8. A modular implant device for the spine, the modular implant device for placement between two adjacent vertebrae, comprising:
   a first member sized to span at least a portion of a distance between the two adjacent vertebrae, the first member including a first body having a first upper surface and a first lower surface and a first opening formed through the body which extends from the first upper surface to the first lower surface, the first opening having a first height;
   a second member sized to span at least a portion of a distance between the two adjacent vertebrae, the second member including a second body having a second upper surface and a second lower surface and a second height, the second height being less than the first height, the second body being sized and configured to fit fully within the first opening;
   a first end cap having a first insert portion that fits within the first opening and a first rim portion which extends upwards from the insert portion, wherein the first member further includes an inwardly extending ridge positioned inside of the first opening, the inwardly extending ridge including an upwardly facing shoulder surface which engages with a lower surface of the first insert portion when the first inset portion is positioned in the first opening.

9. The modular implant device of claim 8, wherein a cross-sectional dimension of the first rim portion is greater than a cross-sectional dimension of the first member.

10. The modular implant device of claim 8, wherein the first member comprises a first material and the second member comprises a second material, wherein the first and second materials are the same material.

11. The modular implant device of claim 8, wherein the first member comprises a first material and the second member comprises a second material, wherein the first and second materials are different materials.

12. The modular implant device of claim 8, wherein at least one of the first and second members comprise silicon nitride.

13. The modular implant device of claim 8, wherein at least a portion of the modular implant device comprises silicon nitride.

14. A modular implant device for the spine, the modular implant device for placement between two adjacent vertebrae, comprising:
   a first member sized to span at least a portion of a distance between the two adjacent vertebrae, the first member including a first body having a first upper surface and a first lower surface and a first opening formed through the body which extends from the first upper surface to the first lower surface, the first opening having a first height;
   a second member sized to span at least a portion of a distance between the two adjacent vertebrae, the second member including a second body having a second upper surface and a second lower surface and a second height, the second height being less than the first height, the second body being sized and configured to fit fully within the first opening;
   a first end cap having a first insert portion that fits within the first opening and a first rim portion which extends upwards from the insert portion;
   a third member sized to span at least a portion of a distance between the two adjacent vertebrae, the third member having a third height which is less than the first height, and
   the second member further comprising a second opening extending through the second member; wherein the third member is sized to fit fully inside of the second opening.

15. The modular implant device of claim 14, wherein the first member comprises a first material, the second member comprises a second material, and the third member comprises a third material, and the first, second and third materials are all different materials.

16. The modular implant device of claim 14, wherein a cross-sectional dimension of the first rim portion is greater than a cross-sectional dimension of the first member.

17. The modular implant device of claim 14, wherein the first member comprises a first material and the second member comprises a second material, wherein the first and second materials are the same material.

18. The modular implant device of claim 14, wherein the first member comprises a first material and the second member comprises a second material, wherein the first and second materials are different materials.

19. The modular implant device of claim 14, wherein at least one of the first and second members comprise silicon nitride.

20. The modular implant device of claim 14, wherein at least a portion of the modular implant device comprises silicon nitride.

* * * * *